(12) United States Patent
Snodgrass et al.

(10) Patent No.: US 8,633,816 B2
(45) Date of Patent: Jan. 21, 2014

(54) ELECTRONIC REMINDER AND MONITORING SYSTEM FOR HEALTHCARE INFECTION CONTROL PRECAUTIONS

(75) Inventors: David Snodgrass, Jupiter, FL (US); Richard T. Ellison, III, Shrewsbury, MA (US)

(73) Assignees: UltraClenz, LLC, Jupiter, FL (US); University of Massachusetts, Boston, MA (US)

( * ) Notice: Subject to any disclaimer, the term of this patent is extended or adjusted under 35 U.S.C. 154(b) by 21 days.

(21) Appl. No.: 13/434,375

(22) Filed: Mar. 29, 2012

(65) Prior Publication Data

US 2012/0256742 A1      Oct. 11, 2012

Related U.S. Application Data

(60) Provisional application No. 61/470,287, filed on Mar. 31, 2011.

(51) Int. Cl.
*G08B 1/08* (2006.01)
*G08B 23/00* (2006.01)
*A61B 5/00* (2006.01)

(52) U.S. Cl.
USPC ............... 340/539.12; 340/573.1; 340/572.1; 340/286.07; 600/300; 128/903; 128/904

(58) Field of Classification Search
USPC .......................................... 340/539.12, 573.1
See application file for complete search history.

(56) References Cited

U.S. PATENT DOCUMENTS 7,551,092 B1 * 6/2009 Henry .................. 340/573.1
7,898,407 B2 * 3/2011 Hufton et al. ........... 340/539.11

* cited by examiner

*Primary Examiner* — Donnie Crosland
(74) *Attorney, Agent, or Firm* — Lucas & Mercanti, LLP; Peter J. Philips

(57) ABSTRACT

A system and method for monitoring personal protection items of a healthcare worker (gloves, gown, mask and respirator), using a user badge which stores data representing items worn by a worker, wirelessly communicating with the badge before the worker enters a patient zone (such as a patient room, bed area or exam table area), to see whether the worker has the required items. Patient beacons, located near patient room doors, near beds and other locations, store data representing the items required by workers who come in contact with, or close proximity to a patient, and wirelessly communicate with the badge. The patient beacon data can be set for the requirement of the patient, based on patient condition.

24 Claims, 1 Drawing Sheet

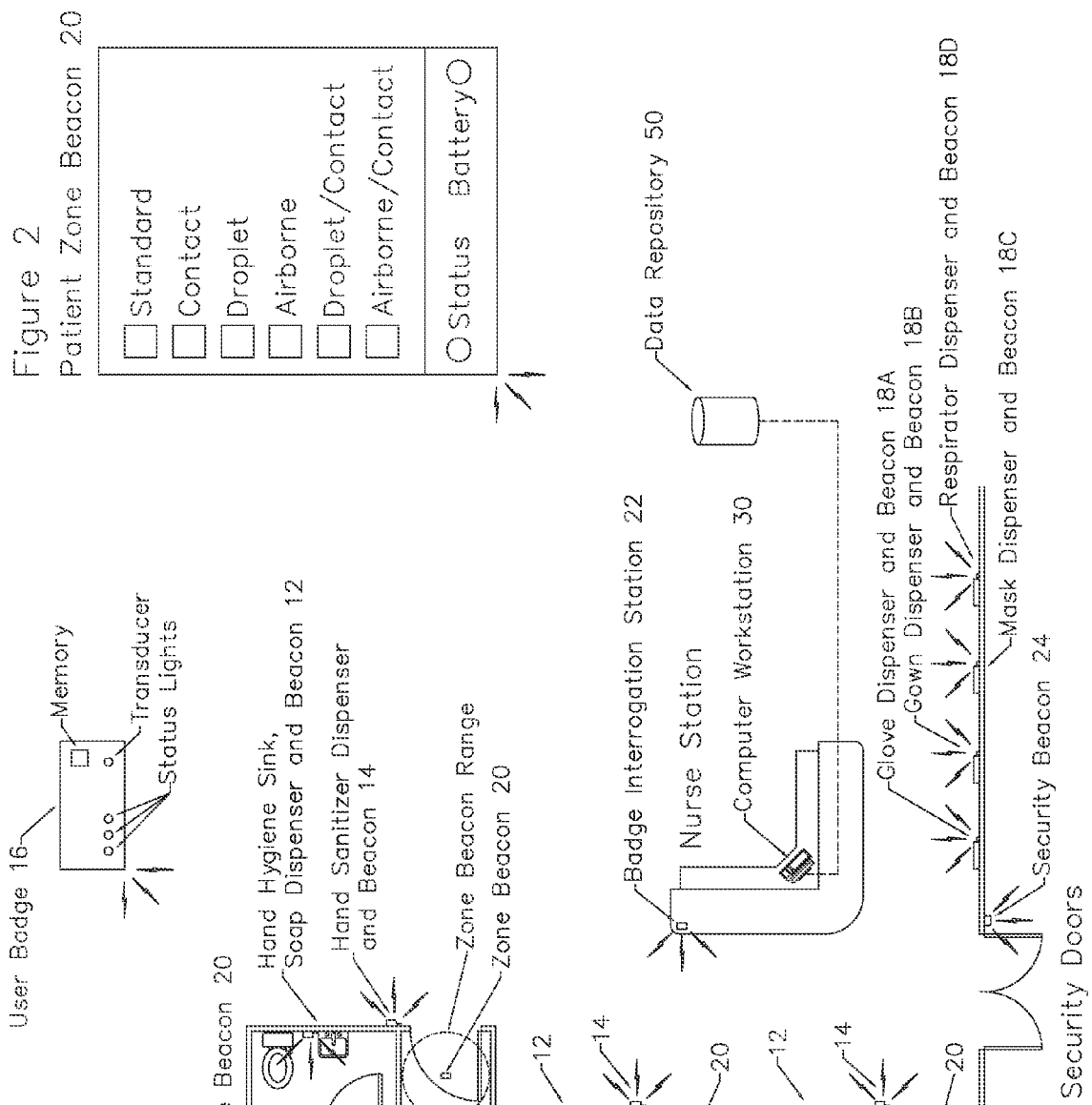

ELECTRONIC REMINDER AND MONITORING SYSTEM FOR HEALTHCARE INFECTION CONTROL PRECAUTIONS

CROSS REFERENCE TO RELATED APPLICATIONS

This application claims priority to U.S. Provisional Application Ser. No. 61/470,287, filed Mar. 31, 2011, which is incorporated by reference herein. This application also incorporates by reference U.S. Application Ser. No, 61/437,466 filed Jan. 28, 2011, U.S. Application Ser. No. 61/486,491 filed May 16, 2011, and U.S. patent application Ser. No. 13/213,823 filed Aug. 23, 2011.

GOVERNMENT RIGHTS

This invention was made with Government support under Grant No. RR319882 and entitled "University of Massachusetts Center for Clinical and Translational Science", awarded by the National Institutes of Health. The Government has certain rights in this invention.

FIELD OF THE INVENTION

The present invention is directed to hygiene/infection control precautions reminder and compliance monitoring systems for the healthcare industry.

BACKGROUND OF THE INVENTION

There are three specific infection control practices that are used in US healthcare systems and, depending on an individual patient's medical condition, which may be required individually or in combination. (Siegel J D, Rhinehart E, Jackson M, Chiareilo L, and the Healthcare Infection Control Practices Advisory Committee, 2007 Guideline for Isolation Precautions: Preventing Transmission of Infectious Agents in Healthcare Settings, June 2007 http://www.cdc.gov/ncidod/dhqp/pdf/isolation2007.pdf).
These practices are:
1. Contact precautions: Gloves are required for all workers upon room entry, and gloves and gowns are required for all interactions with a direct patient contact.
2. Droplet precautions: Surgical masks are required for all workers upon room entry.
3. Airborne Infection Isolation precautions: An OSHA approved mask/respirator is required for all workers upon room entry.

SUMMARY OF THE INVENTION

The present invention provides two systems. One system is a personal protective equipment (PPE) monitoring system, and the other is a hand hygiene monitoring (HHM) system.

The PPE system will remind and monitor healthcare workers as to the use of PPE, such as gloves, gowns, masks, and respirators as required for infection control precautions. This will protect healthcare workers directly, and thereby also secondarily protect patients and other healthcare workers from being exposed to infectious pathogens in the healthcare environment. The PPE system will remind, dispense, monitor and report on adherence to healthcare related infection control precautions. Specifically:

Remind: Users will be reminded to put on one or more articles of PPE when the event warrants a specific activity;

Dispense: The system will have the ability to track dispensing of PPE, such as gloves, gowns, masks and respirators of users;

Monitor: The system will have the capacity to monitor individual healthcare worker activity regarding use of PPE and record the activity of the worker when completed; and Report: The system will report compliance or lack of compliance with PPE requirement based on approved infection control standards and predefined protocols.

Preferably, the system should be fairly inexpensive, easy to install, have components which could be powered by battery or wall adapter, have components which are able to communicate without additional data cable installed, provide for communication between components by wireless RF or other wireless technology, be flexible for multiple healthcare environments, meet healthcare standards for RF communications, and meet ADA compliance criteria.

The HHM system can remind, dispense, monitor and report on hand hygiene activity of users.

In addition, to improve healthcare worker acceptance and compliance, each of the PPE and HHM systems have the capacity to interface with hospital access security systems to allow healthcare worker access to secure areas by RF signaling with an infection control precautions badge and/or a card with a card swipe device or wireless REID or the like.

The PPE system can also be used to confirm that healthcare workers are in compliance with the OSHA tuberculosis standard for airborne precautions.

The PPE and HHM systems could be integrated together, or function as stand-alone systems. The systems will not only encompass hand hygiene but other infection prevention events that contribute to the infections of patients in the healthcare environment.

The HHM system will remind, dispense, monitor and report the hand hygiene activity of healthcare workers with enhancements geared towards hand hygiene in a healthcare setting as well as adherence to other healthcare related infection control precautions.

The PPE and HHM systems will remind healthcare workers to perform either or both activities prior to putting the patient or themselves at risk. The inventive systems provide for reminding, monitoring and reporting key events.

Users will be reminded to wash or sanitize their hands or put on personal protection items when the event warrants a specific activity. The systems will have the capacity to monitor individual healthcare worker activity and record the activity of the worker when completed. The systems will report compliance or tack of compliance based on approved infection control standards and predefined protocols.

Each system contemplates use of badges for healthcare workers, and the design of these badges permit functioning in both systems.

The system can manage droplet and airborne precautions, and provide reminders for gowns, masks, N95 respirators, and powered air purifying respirators (PAPRs) that can optionally be turned off.

The invention provides a sanitation compliance monitoring system for a health care environment having patients in patient zones, comprising badges wearable by persons, said badges having memory for storing personal protection status data representing personal protections implemented by a person, said badges also having a wireless transmitter/receiver; patient zone beacons, each associated with a different respective patient zone, each patient zone beacon storing data representing personal protection requirements of persons required by the zone based on the condition of the patient in the zone, and having a wireless transmitter/receiver; wherein the patient zone beacon communicates with each badge and checks whether the personal protection status data in the badge indicates that the person wearing the badge has the personal protections required by the patient zone beacon, and wherein the badge produces a warning signal if the person's personal protection is not compliant.

The invention provides a sanitization compliance monitoring method for a health care environment having patients in patient zones, comprising equipping persons with badges, said badges having memory for storing personal protection status data representing personal protections implemented by a person, said badges also having a wireless transmitter/receiver; before a person wearing a badge enters a patient zone, checking to see whether the person has required personal protection required by that patient zone, by using wireless communication, between the badge and a patient zone beacon associated with that patient zone which beacon stores data representing personal protection requirements of that patient; wherein the badge produces a warning signal if the person's personal protection is not compliant with the personal protection requirements of the patient.

BRIEF DESCRIPTION OF THE DRAWING

FIG. 1 is a block diagram showing the components according to the invention; and FIG. 2 shows a patient zone beacon with selection switches to select the PPE requirements of the room as determined by the room patient.

DETAILED DESCRIPTION OF THE PREFERRED EMBODIMENT

A preferred embodiment will now be described, but the preferred embodiment is but one example, and the invention is not limited to the preferred embodiment.

The invention provides a sanitization compliance monitoring system for a health care environment having patients in patient zones, comprising badges wearable by persons, said badges having memory for storing personal protection status data representing personal protections implemented by a person, said badges also having a wireless transmitter/receiver; patient zone beacons, each associated with a different respective patient zone, each patient zone beacon storing data representing personal protection requirements of persons required by the zone based on the condition of the patient in the zone, and having a wireless transmitter/receiver; wherein the patient zone beacon communicates with each badge and checks whether the personal protection status data in the badge indicates that the person wearing the badge has the personal protections required by the patient zone beacon, and wherein the badge produces a warning signal if the person's personal protection is not compliant.

The personal protection status data may represent at least one of gloves, gown, mask and respirator personal protection items. The badge memory may also store data indicating whether a user has been fitted to wear a particular personal protection item, and wherein a warning signal is produced if the personal protections requirements require the particular personal protection item, regardless of whether the user possesses the particular personal protection item. The particular personal protection item may be a respirator. The system may further include a central unit for wirelessly communication with patient zone beacons, and wherein the patient room beacons transmit the identification signal of the badge, and the current personal protection status data of the badge, to the central unit. The wireless communication may include time stamp data indicating the date and time of each communication of data between a badge with a patient zone beacon. The badge may include at least one visual indicator to indicate whether the personal protection status data stored in the badge is compliant with the personal protections required by the patient zone. The system may further include at least one personal protection item dispenser for dispensing at least one type of personal protection item, and for communicating a personal protection dispensing signal to a badge indicating the item dispensed, and wherein the badge personal protection status data is changed in response to said personal protection dispensing signal. The patient zone beacon may be associated with a patient room. The patient zone beacon may be associated with a patient bed. The patient zone beacon may be associated with a patient exam table. The badge memory may store hand hygiene status information representing hand hygiene events indicating the time of the last hand hygiene event of the user, and wherein the badge produces a warning signal in response to the badge's user not conducting a hand hygiene event between different patient zones.

The invention provides a sanitization compliance monitoring method for a health care environment having patients in patient zones, comprising equipping persons with badges, said badges having memory for storing personal protection status data representing personal protections implemented by a person, said badges also having a wireless transmitter/receiver; before a person wearing a badge enters a patient zone, checking to see whether the person has required personal protection required by that patient zone, by using wireless communication, between the badge and a patient zone beacon associated with that patient zone which beacon stores data representing personal protection requirements of that patient; wherein the badge produces a warning signal if the person's personal protection is no compliant with the personal protection requirements of the patient.

The personal protection status data may represent at least one of gloves, gown, mask and respirator (either N95 or PAPR) personal protection items. The badge memory may also store data indicating whether a user has been fitted to wear a particular personal protection item, and wherein a warning signal is produced if the personal protections requirements require the particular personal protection item, regardless of whether the user possesses the par color personal protection item. The particular personal protection item may be a respirator. The method may further include wirelessly transmitting the results of the checking, and an identification signal identifying the badge, to a central unit. The wirelessly transmitting may include communicating time stamp data indicating the date and time of each communication of data between a badge with a patient zone beacon. The method may further include the step of providing a visual indicator on the badge to indicate whether the personal protection status data stored in the badge is compliant with the personal protections required by the patient zone. The method may further include the step of changing the personal protection data in the badge in response to the person obtaining at least one personal protection item from a personal protection item dispenser which dispenses at least one type of personal protection item, by wireless communication between the badge and personal protection item dispenser. The patient zone may be associated with a patient room. The patient zone may be associated with a patient bed. The patient zone may be associated with a patient exam table. The method may include the step of storing in badge memory hand hygiene status information representing hand hygiene events indicating the time of the last hand hygiene event of the user, and wherein the badge produces a warning signal in response to the badge's user not conducting a hand hygiene event between different patient zones.

General System Components

Referring to FIG. 1, the overall system 10 will consists of at least one an electronic touch-free hand wash or sanitization station 12, at least one electronic touch-free sanitation station 14, at least one electronic user badge (active) 16, at least one electronic protective equipment dispenser 18 (separate dispensers 18A-D for gloves, gowns, masks and respirators being shown), beacons 20 to monitor patient zones (both room entry zones, individual patient bed/exam table), badge interrogation stations 22, security beacons 24, and a computer workstation 30 to capture and report data on compliance with hand hygiene and infection control precautions.

Hand Hygiene/Infection Control Precaution Beacons

The hand hygiene/infection control precaution beacons are preferably battery operated, with a wall adapter option. The components communicate using preferably infrared (IR) signals, which will extend battery life having a minimum of 90 days, and up to 180 days. The beacons are preferably small, mobile, addressable and programmable easily remotely with different criteria (patient zone, room entry, bed/exam table). As used herein, the term beacon can mean a patient zone beacon, patient room beacon, patient bed beacon, patient exam table beacon, or other region in which the patient is located.

The patient zone beacons (see FIG. 2) provide a way to specify the type of precautions the worker must follow for patient contact, e.g. standard, contact, droplet, airborne, droplet/contact, airborne/contact. Under most conditions, the zone will represent a single patient room, but in select healthcare settings as for example, emergency departments or surgical recovery units, the zone could represent space around a patient bed or stretcher. When a patient is assigned to occupy a zone, appropriate personnel can specify the type of precaution by pressing a switch on the beacon. The switch can illuminate to indicate the type of precautions in effect. The beacon can also be set remotely, either by hard wire connection or wirelessly through a control unit or the like. The display is visible at a distance of up to 10 feet, for example, so that healthcare workers can readily identify the need for precautions prior to entering the zone can confirm the type of protection which is in effect. The beacons can be mounted near a door entry of a room, near a bed or exam table, or any other region in which a patient is located, even temporarily. The patient zone beacons 20 have the ability to be programmed independently with user-defined programming. They also have a visual status light and battery life status tight. They also control direction of signal and signal distance.

Electronic User Badges

The user badges have electronic memory for storing badge identification data uniquely identifying the badge, and personal protection data representing the PPE being worn by the user, and hand hygiene status data. They have a wireless transmitter/receiver.

The electronic user badges 16 are battery operated (with an appropriate off-the-shelf battery life of 30 days, e.g.), have three large multicolor warning lights RED, YELLOW and GREEN (or a single light that can display 3 colors). The badges have a transducer for producing multiple audible sounds. The badges are small and light enough to wear on shirt or lanyard. The badges communicate with patient zone beacons, and communicate the interactions with all beacons to a central station, personal computer and/or data repository, reporting time (day/hr/min/sec) of interaction and current personal protection data status of the badge.

The badge control logic has multiple logic strings with multiple logic markers. A marker indicates whether the user has acquired a particular personal protection item. For example, if the user has a gown, a marker will be stored in badge memory in a data location for a gown. If the user does not have a gown, that data location for the gown will not contain a marker. Similar data locations in memory wilt exist for other items, such as masks, respirators, etc. The badges recognize the different beacons which have their unique beacon addresses and are in communication with the different dispensers 18A-D which dispense gowns, masks, and other items. The number of badge logic states should be sufficient for current use, with capacity for 3 or 4 additional states for upgrades. The logic states include: Clean or standard; Contact precaution activated with or without glove and markers; Droplet precautions activated with or without mask marker, Airborne precaution activated with or without N95/PAPR marker; Contact precautions and Droplet precautions simultaneously; and Contact precautions and Airborne precautions simultaneously.

The badge 16 has a memory which stores up to 24 hours of data. The badges have a steep mode. The badges have the ability to interact with security beacons to allow entrance into restricted areas in healthcare facilities, whether or not patients are located in these restricted areas. A restricted area may be an intensive care unit, surgery room, or quarantine area. The badges have auto shut-off and a shut-off switch.

Sanitizer Stations

The sanitizer stations 14 are ADA compliant, have a battery with wall adapter option, and have a passive IR transmitter/receiver. The stations may have an LCD display and LED lights. The stations dispense product and are able to have 2-way wireless communication with badge to tell badge the address of the sanitizer station. The sanitizer/wash stations record each time that it is accessed with a date and time mark, and has the capacity to store data for 1000 activations if a user has used precaution items such that the precaution items are contaminated, the sanitizer station or some other station can signal a badge to remove the precaution item markers, and send a signal to the user that the contaminated precaution items should be removed and disposed.

Hand Wash/Sanitizer Stations

The handwash/sanitizer stations are ADA compliant, easy to install, and have passive IR transmitter/receivers to communicate with the badges and other components. The stations are powered by batteries with AC power backup. The stations have LED lights, dispense handwash soap and/or sanitizer product, which may be in a touch free, non-contact or automatic manner without requiring the user to touch or contact any button or the like. The stations are able to have 2-way communication with badges to tell badges the address of the wash station. Further details of a handwash/sanitizer system may found in the applications incorporated by reference herein. As used herein, handwash and sanitizer are interchangeable, and refer to a hand hygiene procedure whether using soap and water in a sink to perform a handwash, using sanitizer without water and sink, or some other hand hygiene procedure.

Badge/Sanitizer Interrogation Stations

These stations 22 download data from badges and sanitizer stations. The stations have wireless radio frequency (RE) transmitter/receivers for wireless data transfer to central data repository 50 to allow placement at unit stations, staff lounges, and timecard locations.

Personal Protective Equipment Dispenser Stations

The dispenser stations 18A-D are ADA compliant and easy to install. The stations have a magnet switch to detect when the sensor door is open. The dispensers are mountable on a wall or transportable on a portable cart or the like, and can be easily relocated. The stations have an LED light and are battery operated, with AC backup. The dispensers are sized to fit industry standard personal protective equipment (glove boxes, gowns, masks, N-95 respirators or PAPR units). They can house either single types of personal equipment or differing combinations of types of personal equipment. They will be able to wirelessly communicate by either magnetic coupling or REID signal with an individual healthcare worker badge. The personal protective equipment will be contained in compartments with either doors with an attached magnetic switch or fixed slit openings with an attached magnetic switch. The dispenser wilt generate an activation signal when a compartment is accessed to remove an item of personal protective equipment. The dispenser will both communicate with the healthcare worker badge to indicate what personal protective equipment has been accessed as well wirelessly transmit a report to the system network with date/time stamp and healthcare worker badge ID. The personal protective equipment stations will be able to be accessed by individuals not wearing a healthcare worker badge, and still record and transmit to the system network with a date/time stamp for each accession. The stations have a beacon which transmits a signal identifying the type of item dispensed to the badge, and the address of the dispenser. The badge will then store an appropriate mark in memory representing that the user has the item dispensed.

Security Beacons

The security beacons 24 monitor and allow healthcare workers to enter a secure area of a healthcare environment using a badge without the need to use an ID badge card swipe system. These beacons have the ability to read badge identification numbers of each badge. These beacons interface with security badge swipe systems.

Description of Operation

Hand Hygiene Reminder System

A healthcare worker should approach a patient only when his badge shows a green light, which shows that the worker is fully compliant with the hand hygiene requirements. A healthcare worker enters room from a hallway where the badge has been showing a green light. Upon entering the room the electronic badge light turns yellow and an audible alarm is turned on that will continue indefinitely. When the healthcare worker either washes their hands at a hand wash station or uses a hand sanitizer, the electronic badge light returns to green, and the audible alarm is turned off. The worker can then approach a patient where the badge remains green. Should the healthcare worker approach a patient with the badge still in the yellow state, after 30-45 seconds the badge light will change to red, and a new audible alarm will begin to signal. Once the worker finishes with a patient the worker can then leave the room where the badge light will again change to yellow and an audible alarm is initiated to remind the worker to wash his/her hands.

Operation

When a healthcare worker wearing a badge enters a room, the badge records that it was hit by a beacon signal and records the beacon address. The badge status will change from "clean" status to "intermediate" or "yellow" status which will then remind the worker that the worker needs to sanitize their hands by producing a series of audible beeps and a visual yellow light on the badge meaning "caution" or a state of caution. When the worker sanitizes their hands, either by a handwash or using sanitizer, the hand hygiene event interaction is stored in badge memory and the badge status is returned to "clean" and the green status light appears. The badge status is set to not respond to a doorway beacon for 15 seconds, but can still immediately respond to a bed beacon.

If the worker does not sanitize his/her hands and he/she approaches the bed/exam table beacon of a patient with the badge in the intermediate status (a yellow status light flashing), then the badge will status will change to alarm status, and a red light would appear that says the worker is out of compliance in an "alarm" state. The badge would then record this beacon interaction as being out of compliance. If the worker has sanitized his/her hands and the badge is in a "clean" or green status when the interaction with the bed beacon occurs, the badge will remain in a clean status and the badge would store the interaction with a bed beacon as being in compliance. The worker is permitted to move in and out of contact with the bed beacon and remain in a clean status as long as the worker does not interact with the room entry beacon. The worker can then either perform hand sanitization in the room and exit the room with the badge remaining in a clean status, or exit the room directly. In the latter situation, the badge status would revert to intermediate state, and the worker will be reminded to perform hand hygiene in a station outside the patient room.

If a worker is going from patient room to patient room (or patient zone to patient zone), and the worker has just sanitized his/her hands within the 15 second delay period, as soon as he/she enters a second patient room (or zone), the interaction with the second room/zone beacon will be recorded but the badge will remain in the green state. If the badge was in the intermediate (yellow) or red alarm state when the worker enters a second zone/room and the interaction with the second zone/door beacon would be recorded, the badge would remain in the same state (either intermediate or alarm).

Infection Precaution Room (Contact, Droplet, Airborne)

The room entry location tag and the required precautions for that patient zone/room can be set locally by unit staff to require contact, droplet, or airborne precautions atone or in combination, or be set by a central station and communicated wirelessly to the patient zone/room/bed beacon.

A. Contact Precautions

Based on the condition of the patient in the zone, room, bed or exam table (or other conditions), when the zone tag is set for "contact precautions," meaning that the user must be wearing gloves, and possibly also a gown, the zone beacon wilt transmit a signal to the badge that the room is set for "contact precautions" and a "glove access" mark (and possibly also a "gown access" mark) stored in the badge is required. If the user, based on his badge status, has not met these requirements, the badge flashes yellow, and the badge will also emit an audible warning alarm. If no action is taken within a time period of say 20 seconds, the badge state will change from yellow to red, and emit a red alarm signal. The worker should exit the zone to get gloves, and also a gown if required, from the electronic personal equipment dispenser. When the worker removes gloves or gown from the appropriate dispenser 18, and the dispenser beacon sends out a signal to mark the badge with the respective item(s) taken, and the red light stops flashing. The worker's badge receives and stores a "glove" marker if gloves were taken and a "gown" marker if a gown was taken. The glove and gown access marks are different. The worker can then walk into the patient's zone and the badge again is signaled by the zone beacon. When the badge has a glove marker, it will remain in a clean contact precaution state but will add a glove—room entry encounter. When the worker then comes in range of a zone beacon in the clean contact precaution state, the badge will be checked for the presence of a "gown access" mark. If there is no gown access mark stored in the badge, the badge will switch to an intermediate contact precaution status (a yellow status light flashing), and if the worker stays in range of the zone beacon for 15 seconds it will then change to an alarm status, and a red alarm light would appear. The badge will also then record this beacon interaction indicating that the badge is out of compliance. If the worker's badge has a "gown access" mark when he/she interacts with the bed beacon, the badge will remain in a "clean" or "green" status and the badge would store the interaction with a zone beacon as being in compliance. If the worker interacts with the zone beacons, but steps out of range of the zone beacon within 15 seconds, the badge will revert to the "clean" or "green" contact precaution status.

Once finished interacting with the patient either after being in contact with a bed beacon or not, the worker should remove his/her gloves and gown. The worker should then sanitize his/her hands and exit the room. If the worker sanitizes his/her hands in the patient room, the badge will again be set to a delay state for a time period of e.g., 15 seconds, so that the badge does not change to an "intermediate" or "alarm" state when interacting with the room entry beacon. The use of either a hand sanitizer/wash station will signal the user's badge, and thus the user, to remove glove and gown marks. If the worker has not sanitized his/her hands prior to the exit interaction with the room entry beacon, the badge state will change to the standard room intermediate status to remind the worker to sanitize his/her hands.

B. Droplet Precautions

The operation and logic for a zone or room set for a "droplet precaution" room is generally similar to that as for "contact precaution," except that the item being checked for is a mask. As the worker enters the room the room beacon interrogates the badge for a "droplet access" mark to see whether the user is wearing a mask. If the badge is not set for "droplet access," the badge issues a warning alarm. The badge will flash yellow and emits a quiet audible alarm for a time period, of e.g., 30 seconds, to remind worker to obtain a surgical mask from the electronic personal equipment supply dispenser. When the worker removes a surgical mask from a mask dispenser 18C, a beacon associated with that dispenser sends out a signal to mark the badge as "droplet access" approved and the alarm is turned off.

Once the beacon determines the badge has "droplet access" for infection control precautions requiring a droplet mask, it will again stay yellow, warning the worker to sanitize their hands. Once the worker sanitizes his/her hands the badge will turn green and the worker can then approach the patient. The logic will follow that for a standard patient room.

Once the worker has finished interacting with the patient, either after being in contact with a bed beacon or not, the worker will need to sanitize his/her hands and exit the room. If the worker sanitizes his/her hands in the patient room, the badge will again be set to a delay state, of 15-30 seconds, e.g., so that the badge does not change to an intermediate or alarm state when interacting with the room entry beacon. When the worker leaves the room and interacts with the room entry beacon signaling "droplet precautions," if the badge is in the "clean droplet precaution" status with a surgical mask access mark, the mask access marks are cleared from the badge register, and the badge returns to a standard clean state if the worker has not has sanitized his/her hands prior to the exit interaction with the room entry beacon, the badge would change into the standard room intermediate status to remind the worker to sanitize his/her hands.

C. Airborne Precautions

For airborne precautions, the operation and logic is generally similar to that as for droplet precautions, except that the item being checked for is a N95 respirator or a PAPR. For healthcare workers to use an N95 respirator, they need to have been fit tested for these masks. At the time the healthcare worker was fit tested, the system would assign an N95 approval to the worker's badge. When that worker obtained an N95 badge from a supply cabinet, the badge would be signaled to stay in a "clean airborne" state that would remain in place for 12 hours, independent of any subsequent interactions with an airborne room entry beacon.

If a healthcare worker had not been fit tested for an N95 badge, and been assigned approval, his/her badge would not respond to the N95 supply cabinet beacon as having "clean airborne" approval, even if he/she has been issued a N95 mask. Instead the worker could don a PAPR unit, receiving a signal similar to that of a surgical mask dispenser station. All subsequent logic would follow that of a droplet precaution room entry beacon, System Without Functional Bed Beacons This system would operate generally the same as the system without a bed beacon, but would have a different set of logic rules for tracking compliance with hand hygiene, and would not track compliance with the use of gowns for contact precautions.

Standard Hand Hygiene Reminder System

A healthcare worker should only approach a patient with the badge showing a green tight. When a healthcare worker enters room from a hallway when his/her badge shows a green light, the electronic badge light turns "yellow" and an audible alarm is turned on that will continue indefinitely until remedied. To remedy this, the healthcare worker must either wash his/her hands at a hand wash station or use a hand sanitizer. In response, the electronic badge light will return to a "green" state, and the audible alarm is turned off. The worker can then approach a patient and his/her badge will remain green. If the healthcare worker does not wash his/her hands within a certain delay time period, of 30-45 seconds e.g., the badge light will change to red, and a new audible alarm wilt begin to signal. Once the worker finishes with a patient the worker can then leave the room. The badge light will again change to "yellow" and an audible alarm is initiated to remind the worker to wash his/her hands. If the worker does not wash his/her hands within a certain time period, of 30-45 seconds, e.g., the badge light will change to red, and a new audible alarm wilt begin to signal.

Operation

When a healthcare worker enters a patient room with a room entry beacon, the badge records that it received a beacon signal and records the beacon address of the beacon which emitted that signal. The badge status will change from "clean" to "intermediate," and will then remind the worker that they need to sanitize their hands through a series of audible beeps and a visual yellow light on the badge meaning caution. When the worker sanitizes his/her hands, the sanitizing event is stored in badge memory, the badge status is returned to "clean" and the green status light appears. The badge status is set to not respond to a doorway beacon for a delay period, of 15 seconds, e.g. After the worker completes his/her interaction with the patient in the room, the worker can then either perform hand sanitization in the room and exit the room with the badge remaining in a clean status, or exit the room directly. In the latter situation, the badge status would revert to intermediate, and the worker would be reminded to perform hand hygiene in a station outside the patient room.

The badge records each time it interfaces and communicates with a room entry beacon and the badge state when the interaction occurs. It also records the time and badge status whenever it interfaces with a hand sanitizing station. For a healthcare worker to be in compliance with hand hygiene when entering and leaving a patient room the badge should have a record of an interaction with a hand wash/sanitizer station within 15 seconds before or 30 seconds after every encounter with a room entry beacon.

If a worker is going room to room, and the worker has just sanitized his/her hands within the 15 second delay period, when the worker enters a second patient room the interaction with the second doorway beacon will be recorded but the badge will remain in the green state. If the badge is in either the intermediate or red alarm state when the worker enters a second room, the interaction with the second door beacon would be recorded, but the badge would remain in the same state (either intermediate or alarm).

Infection Control Precaution Room (Contact, Droplet, Airborne)

The room entry location tag can be set locally by unit staff to require contact, droplet, or airborne precautions alone or in combination, depending on the medical needs of the patient in the room.

A. Contact Precautions

The room entry beacon will be programmed for gloves, and may also require a gown. The beacon will transmit a signal to the badge that the room is set for "contact precautions" requiring gloves, and also possibly a gown. If the worker does not meet the requirements of the room, access is not permitted, and the badge flashes red and yellow lights.

When a worker enters the room and interacts with the doorway beacon, the badge will assess itself for the presence of glove or gown access mark. If the badge is not set for the proper access marks required, the badge will ring a warning alarm. The badge will flash yellow and then red after a certain time period, of 20 seconds, e.g., and the worker should exit the room to get gloves and possibly also a gown from an electronic personal equipment box, shelf or cart dispenser. When the worker removes a glove or gown from the dispenser, the dispenser will signal the badge to mark the badge as access approved for the item issued, and the red tight will stop flashing. The glove and gown access marks are different. The worker wilt then walk into the patients room and the badge is signaled by the beacon. Once the badge has either a glove or gown marker, it will remain in a clean contact precaution state. Once finished the worker should remove the gloves and gown and then exits the room with same logic structure as with a standard room. The use of either a hand sanitizer/wash station will signal the badge to remove glove and gown marks.

B. Droplet Precautions

The logic for a room set for droplet precaution is generally similar as described above. When a worker enters a room the room entry beacon interrogates the badge for a "droplet access" mark. If the badge is not set for "droplet access," badge rings a warning alarm. The badge flashes yellow and as a quiet audible alarm for a period of time, e.g., 30 seconds to remind worker to obtain a surgical mask from an electronic personal equipment supply box, shelf or cart dispenser. When the worker removes the surgical mask from the mark dispenser 18C, a dispenser beacon sends out a signal to mark the badge as "droplet access" approved.

If the room entry beacon determines that the badge has access for "droplet precautions" requiring a droplet mask, it will still stay yellow, warning the worker to sanitize their hands. Once the worker sanitizes their hands the badge will turn green and the worker can approach the patient. The logic will follow that for a standard patient room.

Once the worker has finished interacting with the patient, either after being in contact with a bed beacon or not, the worker needs to sanitize his/her hands and exit the room. If the worker sanitizes his/her hands in the patient room, the badge will again be set to a delay state so that it does not change to an intermediate or alarm state when interacting with the room entry beacon. When the worker leaves the room and interacts with the room entry beacon signaling "droplet precautions" needed, if the badge is in the "clean droplet precaution" status state with a surgical mask access mark, the mask access marks are cleared from the badge register, and the badge returns to a standard clean state. If the worker had sanitized his/her hands prior to the exiting the room and interacting with the room entry beacon, the badge status would change to the standard room intermediate status to remind the worker to sanitize their hands.

C. Airborne Precautions

For airborne precautions, the logic would remain generally similar to that for droplet precautions. However, for healthcare workers to use an N95 respirator, they need to have been fit tested for these masks. At the time a healthcare worker is fit tested, the system would assign an N95 approval to the worker's badge. When that worker obtained an N95 badge from a supply cabinet, the badge would be signaled to stay in a clean airborne state that would remain in place for 12 hours, independent of any subsequent interactions with an airborne room entry beacon.

If a healthcare worker had not been fit tested for an N95 badge, and been assigned approval. Their badge would not respond to the N95 supply cabinet beacon. Instead they could don a PAPR unit, receiving a signal similar to that of a surgical mask dispenser station. All subsequent logic would follow that of a droplet precaution room entry beacon, System Without Functional Bed Beacons This system would operate generally the same as the system without a bed beacon, but would not track compliance with the use of gowns for contact precautions.

Monitoring

Either of these two systems with or without a bed beacon would send date and time stamped signals to a computer database as to the interaction of the healthcare worker badge with the PPE station, doorway entry/exit beacons, and patient bed beacons. These signals would include a reference as to the healthcare worker badge state at the time of interaction. The number of appropriate or non-appropriate interactions that occurred could then be calculated and this information reported to supervising staff.

While preferred embodiments have been shown and described, variations and modifications will occur to those skilled in the art. The present invention is not limited to the preferred embodiments, and the scope is defined only by way of the following claims.

What is claimed is:

1. A sanitization compliance monitoring system for a health care environment having patients in patient zones, comprising:
   badges wearable by persons, said badges having memory for storing personal protection status data representing personal protections implemented by a person, said badges also having a wireless transmitter/receiver;
   patient zone beacons, each associated with a different respective patient zone, each patient zone beacon storing data representing personal protection requirements of persons required by the zone based on the condition of the patient in the zone, and having a wireless transmitter/receiver;

wherein the patient zone beacon communicates with each badge and checks whether the personal protection status data in the badge indicates that the person wearing the badge has the personal protections required by the patient zone beacon, and wherein the badge produces a warning signal if the person's personal protection is not compliant.

2. The system according to claim 1, wherein the personal protection status data represents at least one of gloves, gown, mask and respirator personal protection items.

3. The system according to claim 1, wherein the badge memory also stores data indicating whether a user has been fitted to wear a particular personal protection item, and wherein a warning signal is produced if the personal protections requirements require the particular personal protection item, regardless of whether the user possesses the particular personal protection item.

4. The system according to claim 3, wherein the particular personal protection item is a respirator.

5. The system of claim 1, further including a central unit for wirelessly communication with patient zone beacons, and wherein the patient room beacons transmit the identification signal of the badge, and the current personal protection status data of the badge, to the central unit.

6. The system of claim 1, wherein the wireless communication includes time stamp data indicating the date and time of each communication of data between a badge with a patient zone beacon.

7. The system of claim 1, wherein the badge includes at least one visual indicator to indicate whether the personal protection status data stored in the badge is compliant with the personal protections required by the patient zone.

8. The system of claim 1, further including at least one personal protection item dispenser for dispensing at least one type of personal protection item, and for communicating a personal protection dispensing signal to a badge indicating the item dispensed, and wherein the badge personal protection status data is changed in response to said personal protection dispensing signal.

9. The system of claim 1, wherein the patient zone beacon is associated with a patient room.

10. The system of claim 1, wherein the patient zone beacon is associated with a patient bed.

11. The system of claim 1, wherein the patient zone beacon is associated with a patient exam table.

12. The system of claim 1, wherein the badge memory stores hand hygiene status information representing hand hygiene events indicating the time of the last hand hygiene event of the user, and wherein the badge produces a warning signal in response to the badge's user not conducting a hand hygiene event between different patient zones.

13. A sanitization compliance monitoring method for a health care environment having patients in patient zones, comprising:

equipping persons with badges, said badges having memory for storing personal protection status data representing personal protections implemented by a person, said badges also having a wireless transmitter/receiver;

before a person wearing a badge enters a patient zone, checking to see whether the person has required personal protection required by that patient zone, by using wireless communication, between the badge and a patient zone beacon associated with that patient zone which beacon stores data representing personal protection requirements of that patient;

wherein the badge produces a warning signal if the person's protection is not compliant with the personal protection requirements of the patient.

14. The method according to claim 13, wherein the personal protection status data represents at least one of gloves, gown, mask and respirator (either N95 or PAPR) personal protection items.

15. The method according to claim 13, wherein the badge memory also stores data indicating whether a user has been fitted to wear a particular personal protection item, and wherein a warning signal is produced if the personal protections requirements require the particular personal protection item, regardless of whether the user possesses the particular personal protection item.

16. The method according to claim 15, wherein the particular personal protection item is a respirator.

17. The method of claim 13, further including wirelessly transmitting the results of the checking, and an identification signal identifying the badge, to a central unit.

18. The method of claim 17, wherein the wirelessly transmitting includes communicating time stamp data indicating the date and time of each communication of data between a badge with a patient zone beacon.

19. The method of claim 13, further including the step of providing a visual indicator on the badge to indicate whether the personal protection status data stored in the badge is compliant with the personal protections required by the patient zone.

20. The method of claim 13, further including the step of changing the personal protection data in the badge in response to the person obtaining at least one personal protection item from a personal protection item dispenser which dispenses at least one type of personal protection item, by wireless communication between the badge and personal protection item dispenser.

21. The method of claim 13, wherein the patient zone is associated with a patient room.

22. The method of claim 13, wherein the patient zone is associated with a patient bed.

23. The method of claim 13, wherein the patient zone is associated with a patient exam table.

24. The method of claim 13, including the step of storing in badge memory hand hygiene status information representing hand hygiene events indicating the time of the last hand hygiene event of the user, and wherein the badge produces a warning signal in response to the badge's user not conducting a hand hygiene event between different patient zones.

* * * * *